(12) United States Patent
Feiner et al.

(10) Patent No.: US 7,458,372 B2
(45) Date of Patent: Dec. 2, 2008

(54) INHALATION THERAPY DEVICE

(75) Inventors: Franz Feiner, Munich (DE); Markus Borgschulte, Munich (DE); Wolfgang Achtzehner, Alling (DE); Eduard Kunschir, Munich (DE); Joseph Lass, Munich (DE)

(73) Assignee: PARI Pharma GmbH, Starnberg (DE)

( * ) Notice: Subject to any disclaimer, the term of this patent is extended or adjusted under 35 U.S.C. 154(b) by 385 days.

(21) Appl. No.: 10/533,430

(22) PCT Filed: Oct. 30, 2003

(86) PCT No.: PCT/EP03/12076

§ 371 (c)(1),
(2), (4) Date: Dec. 28, 2005

(87) PCT Pub. No.: WO2004/039442

PCT Pub. Date: May 13, 2004

(65) Prior Publication Data

US 2006/0102172 A1    May 18, 2006

(30) Foreign Application Priority Data

Oct. 30, 2002 (DE) .............................. 102 50 625

(51) Int. Cl.
*A61M 11/00* (2006.01)
(52) U.S. Cl. .............................. 128/200.14; 128/200.16
(58) Field of Classification Search ............ 128/200.16, 128/200.14, 200.31, 203.12, 203.16
See application file for complete search history.

(56) References Cited

U.S. PATENT DOCUMENTS

| | | | |
|---|---|---|---|
| 3,812,854 A | 5/1974 | Michaels et al. | |
| 3,948,264 A | 4/1976 | Wilke et al. | |
| 4,319,155 A | * 3/1982 | Nakai et al. | 310/316.01 |
| 4,868,521 A | 9/1989 | Konrad | |
| 5,551,416 A | * 9/1996 | Stimpson et al. | 128/200.16 |
| 6,539,937 B1 | * 4/2003 | Haveri | 128/200.21 |
| 6,540,154 B1 | 4/2003 | Ivri et al. | |
| 2005/0034719 A1 | 2/2005 | Feiner et al. | |
| 2005/0056274 A1 | 3/2005 | Kunschir | |

FOREIGN PATENT DOCUMENTS

| | | |
|---|---|---|
| DE | 3013964 C2 | 10/1981 |
| DE | 3118502 A1 | 11/1982 |
| DE | 29501569.1 U1 | 4/1995 |
| DE | 19953317 C1 | 2/2001 |
| EP | 0303944 A1 | 2/1989 |
| EP | 1005917 A1 | 6/2000 |
| EP | 1219314 A1 | 7/2002 |
| EP | 1304130 A1 | 4/2003 |
| EP | 1304131 A1 | 4/2003 |
| WO | WO 93/09881 A2 | 5/1993 |
| WO | WO 02/28539 A1 | 4/2002 |
| WO | WO 03/057292 A1 | 7/2003 |

OTHER PUBLICATIONS

International Search Report for Application No. PCT/EP03/12076 dated Jan. 22, 2004.

* cited by examiner

*Primary Examiner*—Steven O Douglas
(74) *Attorney, Agent, or Firm*—Wolf, Greenfield & Sacks, P.C.

(57) ABSTRACT

The invention relates to an inhalation therapy device including a membrane aerosol generator. A detection device is provided for determining whether a liquid to be atomized is available. In the absence of liquid, the activation of the membrane aerosol generator is interrupted and/or a signal is output.

15 Claims, 5 Drawing Sheets

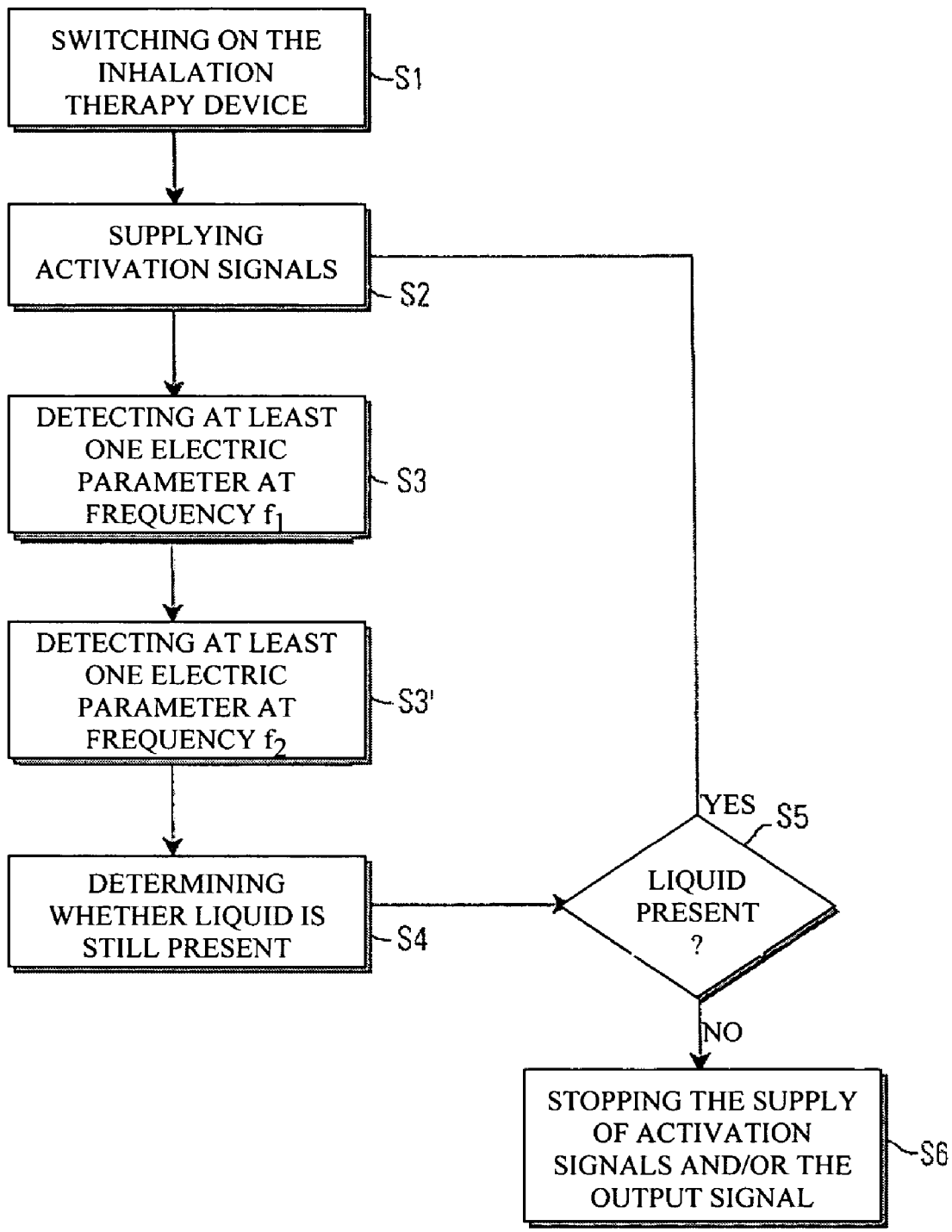

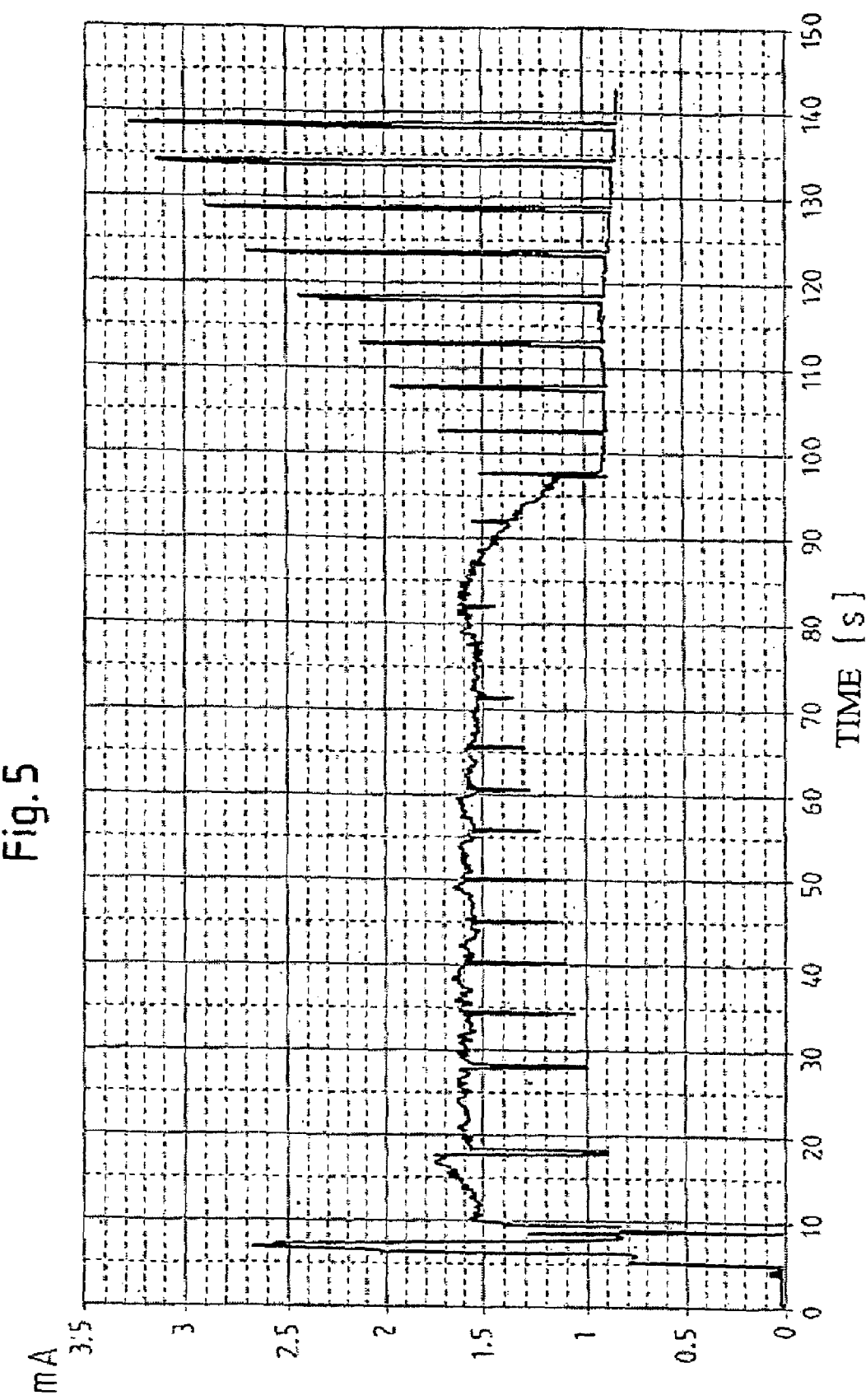

INHALATION THERAPY DEVICE

FIELD OF THE INVENTION

The invention relates to inhalation therapy devices having an oscillatable membrane for nebulising a liquid.

BACKGROUND OF THE INVENTION

Known from the patent specification DE 199 53 317 C1 is an inhalation nebuliser of the type described above. The aerosol membrane generator described therein comprises a cylindrical liquid storage container which is delimited at one end face by a membrane having the shape of a circular disc.

A liquid disposed in the liquid container touches the side of the membrane facing the liquid storage container. DE 199 53 317 C1 furthermore describes an oscillation generator, for example a piezo crystal, which surrounds the membrane in a circular manner and is connected thereto such that the membrane can be caused to oscillate by means of the oscillation generator and an electric drive circuit.

The liquid abutting the membrane on the one side is conveyed through holes in the oscillating membrane to the other side of said membrane and is emitted on this side into the mixing chamber as an aerosol.

Known from the utility model DE 295 01 569 is an ultrasonic liquid nebuliser having a piezo crystal which is caused to oscillate electrically by an oscillator circuit, said oscillator circuit being supplied by a power supply device.

DE 295 01 569 describes an oscillator circuit which comprises a current limiting circuit and which is connected with an electronic temperature limiting circuit that compares a temperature-dependant electric signal occurring at the piezo crystal in a threshold circuit, the comparison signal of which activates a bistable circuit which blocks the oscillator when a limiting temperature in the piezo crystal is reached.

The disclosure of DE 295 01 569 is thereby directed at a protective mechanism for an ultrasonic liquid nebuliser in which the piezo crystal itself causes the liquid to oscillate and is in contact with a comparatively large amount of liquid. The liquid nebuliser described in DE 295 01 569 must furthermore accordingly use large currents in order to cause the large amount of liquid to oscillate.

Constant contact between the piezo crystal and the liquid is necessary owing to these large currents and the resulting large temperature differences in order to prevent destruction of the piezo crystal. If there is no longer any liquid present, the piezo crystal heats up very quickly and is destroyed if the oscillating circuit driving the nebuliser is not switched off immediately.

Only much smaller currents flow in inhalation nebulisers of the type described at the beginning of this document, i.e. in inhalation nebulisers having membrane aerosol generators, and therefore only comparatively small temperature differences occur. In such inhalation nebulisers, the lack of liquid does not directly lead to heat-related damage to the piezoelectric elements. However, if a membrane inhalation nebuliser runs without a load, this can, on rare occasions, cause the membrane to break.

However, it is also necessary in inhalation nebulisers having a membrane generator to reliably detect the presence of a liquid to be nebulised. This is because, on the one hand, the basis for a very high dosage accuracy is thereby created and, on the other hand, it is possible to reliably indicate the end of a therapy session to the patient. Furthermore, by immediately disconnecting the inhalation therapy device, it is possible, for example, to save a battery.

Therefore, the use of a protective mechanism such as described in DE 295 01 569 is not necessary in inhalation nebulisers of the type in question here and is not possible either owing to the much smaller currents and temperature alterations.

SUMMARY OF THE INVENTION

The object of the present invention is therefore to configure an inhalation therapy device having a membrane aerosol generator and a corresponding method such that it is possible to reliably detect whether or not a liquid is present in the liquid reservoir of the inhalation therapy device.

This object is solved by an inhalation therapy device.

Such an inhalation therapy device comprises an oscillatable membrane for nebulising a liquid, an oscillation generating device which has at least one connecting means for supplying an activation signal and by means of which the membrane is caused to oscillate when the activation signal is supplied such that a liquid disposed on one side of the membrane is nebulised through said membrane and is present on the other side of the membrane as an aerosol, and a control means from which an activation signal can be supplied to the at least one connecting means of the oscillation generating device such that the oscillation generating device causes the membrane to oscillate, characterised in that a detection device is provided which detects at least one electric parameter of the oscillatable structure comprising the membrane and the oscillation generating device and which determines the presence of a liquid to be nebulised based on the at least one parameter.

The object is furthermore solved by an inhalation therapy method.

Such an inhalation therapy method for an inhalation therapy device comprises the following steps:

switching on the inhalation therapy device;

supplying activation signals from the control means to the oscillation generating device in order to nebulise the liquid;

detecting at least one electric parameter of the oscillatable structure comprising the membrane and the oscillation generating device; and determining whether or not liquid is still present based on the detected parameter of the oscillatable structure.

The invention enables a greater dosage accuracy of the medicament for the patient, allows the patient to concentrate better on the therapy and increases the user-friendliness of the inhalation therapy device, not least owing to a longer running time during battery operation.

Due to the possibility of determining whether or not liquid is still present, it is possible to automatically switch off the inhalation therapy device and/or to indicate to the patient that there is no medication left in the inhalation therapy device. This can also occur right at the start of a therapy session. However, in particular, the patient does not have to constantly check during the therapy session whether there is any medication left. The user-friendliness of the inhalation therapy device is thereby increased and the therapy is less bothersome for the patient.

Furthermore, detection of the at least one electric parameter means that the battery capacity can be saved and that it can be determined whether there is a bad contact in the inhalation therapy device or whether droplets have formed on the membrane, which affects the nebulising properties of the device. A worse TOR (Total Output Rate) is furthermore also recognised.

However, above all, the accuracy of the dose of the inhalation substance can be improved by the invention and the patient can concentrate better on the therapy, which leads to improved treatment success.

The formation of droplets on the membrane can occur during operation of the inhalation therapy device or the membrane can become clogged. The occurrence of these two phenomena leads to a deterioration of the nebulising properties of the device.

It is, however, possible for the inhalation therapy device to recognise both phenomena since both droplet formation and clogging of the membrane change the at least one detected electric parameter of the oscillatable structure in a characteristic manner. Countermeasures (e.g. switching off the device) can thereby be taken in good time.

BRIEF DESCRIPTION OF THE DRAWINGS

The invention will be described in more detail below by means of embodiments examples as shown in the figures, from which further advantages and features of the invention arise.

FIG. 4 shows a flow diagram which graphically represents a method for determining the presence of liquid in the inhalation device according to a second embodiment example, and FIG. 5 shows an example of the progression over time of a measuring curve of a detected electric parameter when using two different oscillation frequencies for the membrane according to a second embodiment example.

DETAILED DESCRIPTION

Figure 1:
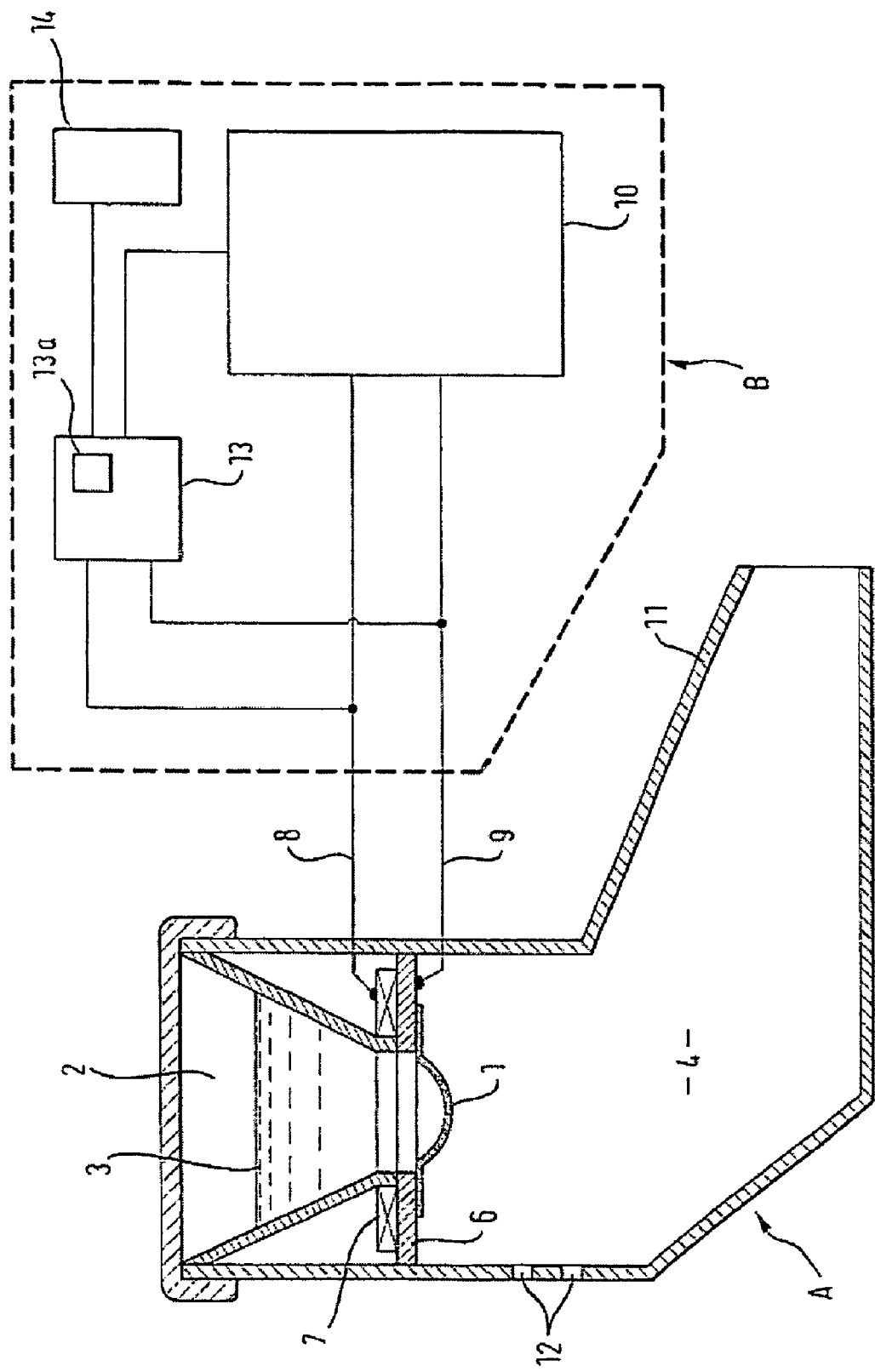
FIG. 1 shows a schematic representation of an inhalation device according to a first embodiment example.
Figure 2:
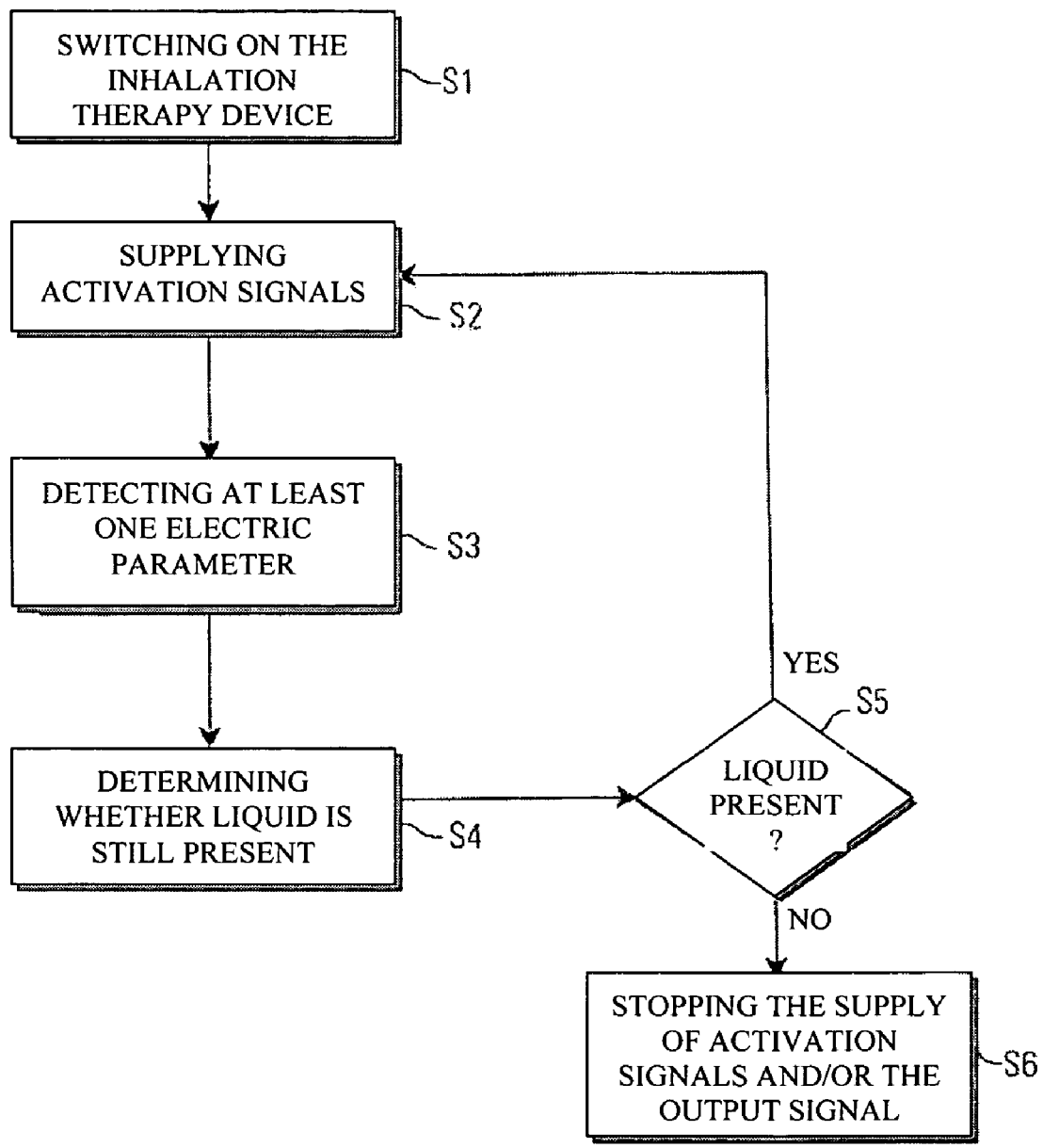
FIG. 2 shows a flow diagram which graphically represents a method for determining the presence of liquid in the inhalation device according to a first embodiment example.

Referring to FIGS. 1 and 2, the invention will now be explained in more detail below by means of a first embodiment.

FIG. 1 shows an inhalation therapy device according to the invention, in which in a nebuliser unit A, a liquid (3) stored in a liquid reservoir (2) is nebulised by means of a membrane (1) into a nebulisation cavity (4).

Nebulisation then occurs when the membrane (1) is caused to oscillate. For this purpose, the membrane (1) is attached to a support unit (6) which supports the membrane (1) and to which an electromechanical transducer unit (7), for example a piezo element, is also attached.

The membrane (1), the support unit (6) and the electromechanical transducer unit (7) are configured in a rotationally symmetrical manner in the embodiment described here and together form an oscillatable structure.

An activation signal of a control means (10) can be supplied to the electromechanical transducer unit (7) via connecting lines (8, 9), said control means being accommodated in a separate control unit B in the embodiment described here. When the activation signal is supplied, the oscillatable structure (1, 6, 7) is caused to oscillate and the liquid (3) is nebulised through the membrane (1).

A patient can inhale the aerosol provided in the nebulisation cavity (4) at the mouthpiece (11) of the nebuliser. So that a sufficient amount of air is supplied, one or more air holes (12) are provided in the housing of the nebuliser, through which ambient air can enter into the cavity (4) during inhalation and out of which the air inhaled by the patient can exit from the cavity (4) during exhalation.

Different electrical properties of the oscillatable structure (1, 6, 7) (e.g. current, voltage, phase shift) are dependant in particular on the capacity of the electromechanical transducer unit (7). The oscillatable structure (1, 6, 7) displays very specific characteristics during nebulisation and during operation without liquid, which are reflected in the electric parameters of the oscillatable structure. The operating states with and without liquid on the membrane can be reliably determined by means of these electric parameters. Current consumption (current), power consumption (power) and the current/voltage phase shift (phase position) are particularly suitable as electric parameters.

In order to detect at least one of the electric parameters, a detection device (13) is provided according to the invention, which is configured and is connected with the oscillatable structure (1, 6, 7) and/or the control means (10) such that the at least one electric parameter is supplied to the detection device (13). For this purpose, the connecting lines (8, 9), for example, are configured such that during operation of the control unit (10), at least one electric parameter of the oscillatable structure (1, 6, 7) is transmitted to the detection device (13) via the connecting lines (8, 9) and can be detected thereby.

The invention is based on the surprising possibility of being able to draw conclusions with regard to the operating state as a result of the detection of at least one electric parameter of the oscillatable structure (1, 6, 7) (e.g. voltage tap, current consumption or the current/voltage phase position at the piezo crystal of the membrane) owing to the characteristics of the oscillatable structure (1, 6, 7) and it can thereby be determined whether or not liquid (3) is still present in the liquid reservoir (2).

Detection of the at least one electric parameter of the oscillatable structure (1, 6, 7) by the detection device (13) can occur continuously or at discrete time intervals.

Determination of the operating state, i.e. determination of whether liquid is present or not, preferably occurs in the detection device (13) by comparing the detected value of the at least one parameter with a value for this parameter stored in said detection device. The detection device (13) comprises, for example, a memory (13a) for this purpose.

If, by comparing a detected value with a stored value, the detection device (13) determines that there is no more liquid (3) stored in the liquid reservoir (2), the detection device (13) then emits, in a preferred embodiment, a signal to the control means (10), which in turn automatically stops the supply of activation signals to the oscillatable structure (1, 6, 7), i.e. automatically switches off the inhalation therapy device.

In an alternative embodiment, the detection device (additionally) emits an optical or audio signal to indicate to the patient that the inhalation therapy device has consumed the stored liquid (3) in the liquid reservoir (2), which signals the end of the therapy session to the patient. For his part, the patient can then switch off the inhalation therapy device if automatic switching off is not provided in addition to the optical/audio signal.

The inhalation therapy device comprises a signal emitting means (14) for emitting the audio/optical signal, which is connected with the detection device (13) (or alternatively the control means).

The audio signal emitted for this purpose can be a short sound signal of 0.5 to 2 seconds in length. These audio signals are, however, not just restricted to notes, rather sound sequences or recorded or synthesised voice signals can also be used.

FIG. 2 shows a flow diagram, by means of which a possible course of a therapy session will now be described.

By switching on the inhalation therapy device (step S1), activation signals are supplied to the oscillatable structure (step S2). Immediately afterwards, the detection device (13) verifies whether the initial conditions for a therapy session exist, i.e. it determines whether liquid (3) is present in the liquid reservoir (2).

More precisely, the detection device (13) detects at least one electric parameter of the oscillatable structure (1, 6, 7) (step S3) and determines, based on the detected value of the at least one electric parameter, whether liquid is present or not (step S4).

For this purpose, the detection device (13) reverts, for example, to empirically determined values for the detected electric parameter, which are stored in a suitable manner in the detection device, for example in the semiconductor memory (13a) shown in FIG. 1, or uses a value of the at least one parameter which was detected in a previous cycle of the loop (see below). This value is stored in a suitable form by the detection deivce (13) for this purpose, for example in the semiconductor memory (13a).

If the presence of liquid is determined by a comparison of the values (step S5), the activation signal continues to be supplied to the oscillatable structure (1, 6, 7); the control sequence then returns to step S2.

If, on the other hand, it is determined in step S5 that no liquid is present, supply of the activation signal to the oscillatable structure (1, 6, 7) is immediately stopped again (step S6). An optical/audio signal can be additionally or alternatively emitted (step S6).

The loop of steps S2 to S5 is performed continuously or at regular intervals (discrete time steps) in order to verify the presence of liquid during the therapy session and, if necessary to stop the supply of the activation signal to the oscillatable structure, and thus to stop nebulisation.

A second embodiment example of the invention will now be explained by means of FIGS. 3 to 5.

Figure 3:
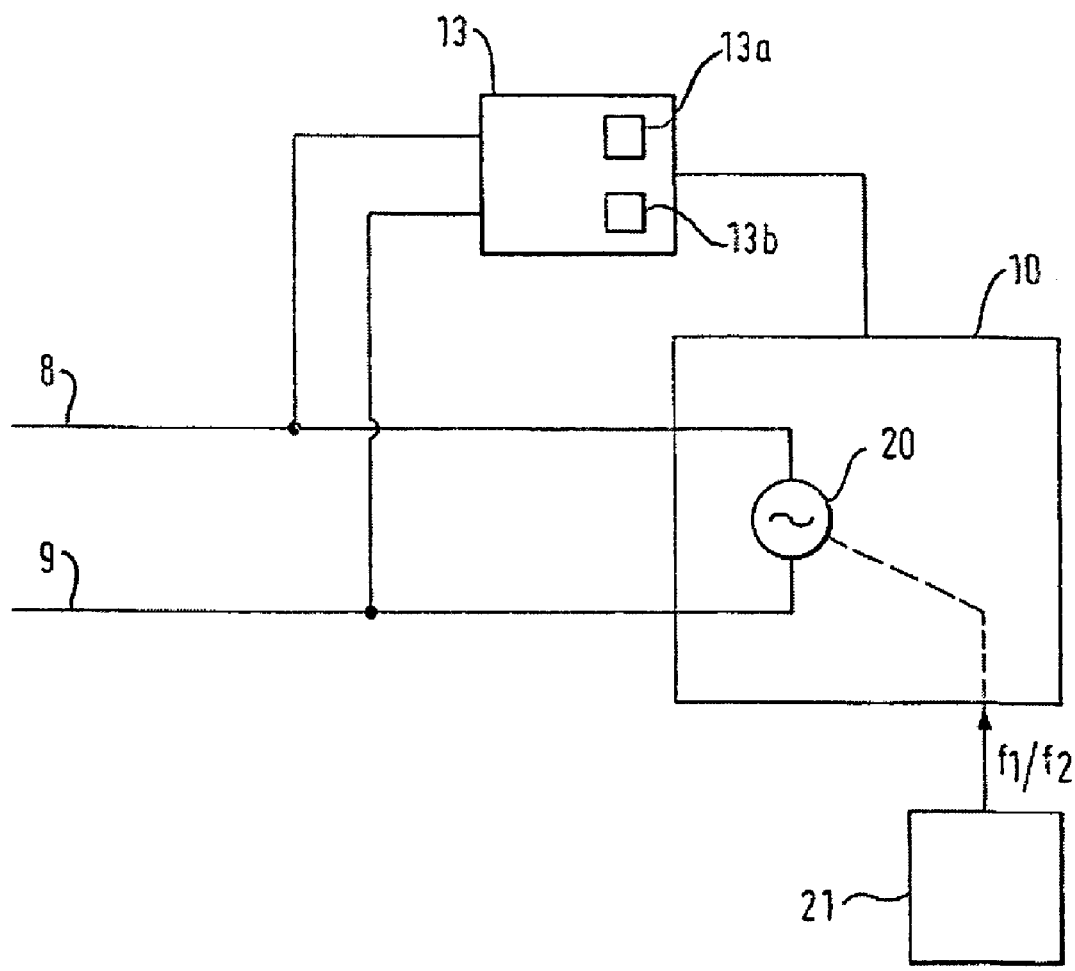
FIG. 3 shows a schematic representation of an inhalation therapy device according to a second embodiment example.

FIG. 3 shows a second embodiment example of an inhalation therapy device, in which at least two different oscillation frequencies for the membrane are generated and are alternatingly supplied to the membrane. The first frequency $f_1$ is the activation frequency which is supplied to the oscillatable structure (1, 6, 7) in order to cause the membrane to oscillate and to nebulise the liquid. The second frequency $f_2$ on the other hand is a frequency used for determining the operating state of the oscillatable structure (1, 6, 7). The time periods in which the second frequency $f_2$ is supplied to the oscillatable structure (1, 6, 7) are typically much shorter than the time periods in which the first frequency $f_1$ is supplied. This is because the second frequency $f_2$ is supplied for measuring purposes and may only disturb the generation of the aerosol to the smallest extent possible.

As shown in FIG. 3, the control unit (10) comprises, for example, an oscillator (20) for this purpose in this second embodiment, which can generate at least two different oscillation frequencies ($f_1$, $f_2$) for the membrane (1).

A switching means (21) switches the oscillator (20) of the control unit (10) between the normal operating frequency $f_1$ and the measuring frequency $f_2$ at predetermined times, the inhalation therapy device nebulising the available liquid during the intervals in which the normal operating frequency $f_2$ is used.

The detection unit (13) stores the detected values of the at least one electric parameter which were detected when using the measuring frequency $f_2$ in order to be able to analyse these measured values also over a longer period of time.

Determination of the operating state, i.e. determination of whether liquid is present or not, then occurs in the detection device (13) either by comparing a value of the at least one parameter that was detected during the normal operating frequency $f_1$ with a value for this parameter that is stored in the detection device (the detection device (13) comprises, for example, a memory (13a) for this purpose), or by evaluating values of an electric parameter that were recorded when using the measuring frequency $f_2$. The operating state can, of course, also be determined by using values of both sets of detected parameters.

It is furthermore also possible to record the values of the electric parameter detected during the normal operating frequency $f_1$ in the detection device (13) (for example in a memory (13b)) in order to also be able to analyse these over a longer period of time.

If the detection device (13) determines that no more liquid (3) is stored in the liquid reservoir (2), the detection device (13) then, in a preferred embodiment, emits a signal to the control means (10), which in turn automatically stops the supply of activation signals to the oscillatable structure (1, 6, 7), i.e. automatically switches off the inhalation therapy device.

Reference is furthermore made to that stated above with regard to the first embodiment example.

FIG. 4 shows a flow diagram, by means of which a possible course of a therapy session according to the second embodiment will now be described.

By switching on the inhalation therapy device (step S1), activation signals having a normal operating frequency $f_1$ are supplied to the oscillatable structure (step S2). Immediately afterwards, the detection device (13) verifies whether the initial conditions for a therapy session exist, i.e. it determines whether liquid (3) is present in the liquid reservoir (2).

More precisely, the detection device (13) detects at least one electric parameter of the oscillatable structure (1, 6, 7) when using the normal operating frequency $f_1$ (step S3) and determines, based on the detected value of the at least one electric parameter, whether liquid is present or not (step S4).

For this purpose, the detection device (13) reverts, for example, to empirically determined values for the detected electric parameter, which are stored in a suitable manner in the detection device, for example in the semiconductor memory (13a) as shown in FIG. 3.

If the presence of liquid is determined (step S5), the activation signal continues to be supplied to the oscillatable structure (1, 6, 7); the control sequence then returns to step S2.

If, on the other hand, it is determined in step S5 that no liquid is present, supply of the activation signal to the oscillatable structure (1, 6, 7) is immediately stopped again (step S6). An optical/audio signal can be additionally or alternatively emitted (step S6).

Following the initialisation step, the loop of steps S2 to S5 is performed continuously or at regular intervals (discrete time steps) in order to verify the presence of liquid during the therapy session and, if necessary to stop the supply of the activation signal to the oscillatable structure and thus nebulisation. Switching between the normal operating frequency $f_1$ and the measuring frequency $f_2$ is thereby carried out at predetermined intervals. The length of the time intervals during which the measuring frequency $f_2$ is used are selected such that the nebulising operation is not disturbed. The time intervals of the measuring frequency are typically smaller by at least a factor of 10.

More precisely, the detection device (13) detects at least one electric parameter of the oscillatable structure (1, 6, 7) during use of the normal operating frequency $f_1$ (step S3) or the measuring frequency $f_2$ (step 3') and determines, based on the detected values of the at least one electric parameter, whether liquid is present or not (step S4).

For this purpose, the detection device (13) reverts, as regards the values detected using the normal operating frequency $f_1$ (step 3), either to empirically determined values for the detected electric parameter, which are stored in a suitable manner in the detection device, for example in the semiconductor memory (13a) as shown in FIG. 3, or uses a value of the at least one parameter which was detected in a previous cycle of the loop. This value was stored for this purpose in a suitable form by the detection device (13), for example in the semiconductor memory (13a).

The detection device (13) evaluates the detected values of the at least one electric parameter of the oscillatable structure (1, 6, 7) that were determined during use of the measuring frequency $f_2$ and were stored in the memory (13b) (step 3') either just like the other measured values or, preferably, over a longer period of time (step 4).

The decision as to whether or not liquid is present can be based in this embodiment example on both types of detected values of the electric parameters. This increases the certitude of the accuracy of the determination of whether or not liquid is present. Furthermore, by observing the course of the measuring curve over a longer period of time, the reliability of the determination of whether or not liquid is present can be further increased.

The invention is, however, not restricted to the use of two frequencies. Several frequencies can be used for the described device.

FIG. 5 shows an example of the progression over time of one of the detected electric parameters when two different frequencies are used for the membrane oscillations.

An example measuring curve can be seen in FIG. 5, which shows the progression of the detected values of the at least one electric parameter of the oscillatable structure (1, 6, 7) according to the second embodiment example. The measured value in the example measuring curve is the current consumption of the oscillatable structure (1, 6, 7) in mA.

The progression over the time period of 0 to approximately 17 seconds can be attributed to the switching-on process and can be disregarded.

It can be seen over the entire range of the measuring curve that in the time intervals in which an activation signal having the operating frequency $f_1$ is applied to the oscillatable structure, a value of approximately 1.6 mA initially occurs, which declines to a value of 0.9 mA between the $80^{th}$ and $97^{th}$ second. This progression of the measuring curve also corresponds to the basic progression of the detected values in an embodiment of the invention in which only the operating frequency $f_1$ is used.

The short time intervals in which an activation signal having the measuring frequency $f_2$ is applied to the oscillatable structure (1, 6, 7) can also be recognised in FIG. 5. These time intervals correspond to the peaks recognisable in FIG. 5, and it is also clear that these time intervals are shorter than the time intervals between the peaks in which the operating frequency $f_1$ is used.

In the time interval between the $15^{th}$ and the $85^{th}$ second, the measured values detected for the operating frequency $f_1$ are in a very narrow range of approximately 1.6 mA. After the $85^{th}$ second, the measuring curve of the values decreases to approximately 0.9 mA for the operating frequency $f_1$. After approximately the $97^{th}$ second, the measured values are again essentially constant.

In the very brief time intervals in which the measuring frequency $f_2$ is used, the peak values are interesting, which increase over the entire progression of the curve. In the time interval between the $15^{th}$ and the $95^{th}$ second, the peak values proceed along a straight line with a first gradient; in the period after the $95^{th}$ second, the peak values of the measured values for the measuring frequency $f_2$ proceed along a straight line with a second gradient which is greater than the first gradient. This change in gradient is a clearly recognisable sign that liquid is lacking on the membrane or on the oscillatable structure (1, 6, 7) of the inhalation therapy device.

Thus, the second embodiment example of the inhalation therapy device according to the invention has two measuring curve progressions, using which the lack of liquid can be determined. This is because, on the one hand, the measuring curve of the values for the operating frequency $f_1$ declines when the liquid has been consumed and, on the other hand, the rate of increase of the peak values of the values determined for measuring frequency $f_2$ changes.

The measuring curve shown in FIG. 5 is just an example and can change for different designs of the inhalation therapy device. In particular, the values and time periods specified can differ depending on the specific configuration of the device.

The invention claimed is:

1. An inhalation therapy device comprising:
   an oscillatable membrane for nebulising a liquid,
   an oscillation generating device having at least one connecting means for supplying an activation signal and by means of which said membrane is caused to oscillate when the activation signal is supplied such that a liquid disposed on one side of the membrane is nebulised through said membrane and is present on the other side of the membrane as an aerosol, and
   a control means from which an activation signal can be supplied to the at least one connecting means of the oscillation generating device such that said oscillation generating device causes the membrane to oscillate,
   wherein
   a detection device is provided which detects at least one electric parameter of an oscillatable structure comprising the oscillatable membrane and the oscillation generating device and which determines the presence of a liquid to be nebulised based on the at least one electric parameter, the at least one electric parameter being a current consumption, a power consumption or a current/voltage phase shift of the oscillatable structure.

2. An inhalation therapy device according to claim 1, wherein the control means alternatingly generates activation signals with at least two different frequencies and the detection device determines the presence of a liquid to be nebulised based on the detected values of the at least one electric parameter at the at least two different frequencies.

3. An inhalation therapy device according to claim 2, wherein at least one first activation signal having a first frequency causes nebulisation of the liquid.

4. An inhalation therapy device according to claim 2, wherein time intervals in which a first activation signal having a first frequency is generated are longer than time intervals in which an activation signal having a second frequency is generated.

5. An inhalation therapy device according to claim 1, wherein detected values are stored for an evaluation over a longer period of time.

6. An inhalation therapy device according to claim 1, wherein if the detection device determines that no liquid is present, said detection device
   prevents supply of activation signals by the control means to the oscillation generating device, and/or
   triggers generation of an optical and/or audio signal by a signal emitting means in order to indicate that no liquid is present.

7. An inhalation therapy device according to claim 6, wherein an emitted audio signal is a short sound signal and/or a sound sequence and/or recorded or synthesised voice signals.

8. An inhalation therapy device according to claim 1, wherein the oscillation generating device comprises an electromechanical transducer unit.

9. An inhalation therapy device according to claim 8, wherein the oscillation generating device comprises a support unit to which the electromechanical transducer unit and the oscillatable membrane are attached.

10. An inhalation therapy device according to claim 1, wherein an energy supply unit for the inhalation device is integrated in the control means.

11. An inhalation therapy method for an inhalation therapy device according to claim 1, comprising the following steps:
    switching on the inhalation therapy device;
    supplying activation signals from the control means to the oscillation generating device in order to nebulise the liquid;
    detecting at least one electric parameter of the oscillatable structure comprising the membrane and the oscillation generating device; and
    determining whether or not liquid is still present based on the detected parameter of the oscillatable structure, the at least one electric parameter being the current consumption, the power consumption or the current/voltage phase shift.

12. An inhalation therapy method for an inhalation therapy device according to claim 2, comprising the following steps:
    switching on the inhalation therapy device;
    supplying activation signals having at least two different frequencies from the control means to the oscillation generating device, the liquid being nebulised at at least one frequency;
    detecting values of at least one electric parameter of the oscillatable structure comprising the membrane and the oscillation generating device at the at least two different frequencies; and
    determining whether or not liquid is present based on the values of the detected parameter of the oscillatable structure at at least one of the at least two different frequencies.

13. An inhalation therapy method for an inhalation therapy device according to claim 11, wherein said method further comprises the following steps:
    continuing to supply the activation signals from the control means to the oscillation generating device in order to continue nebulisation of the liquid if it is determined that liquid is present; and
    stopping the supply of activation signals from the control means to the oscillation generating device and/or emission of an optical and/or audio signal if it is determined that no liquid is present.

14. An inhalation therapy device according to claim 2, wherein the time intervals in which a first activation signal having a first frequency is generated are longer, by at least a factor of 10, than the time intervals in which an activation signal having a second frequency is generated.

15. An inhalation therapy device according to claim 1, wherein the oscillation generating device comprises a piezoelectric element.

* * * * *